United States Patent
Kuzma

[11] Patent Number: 6,070,105
[45] Date of Patent: May 30, 2000

[54] MODIOLUS-HUGGING COCHLEAR ELECTRODES

[75] Inventor: Janusz A. Kuzma, Englewood, Colo.

[73] Assignee: Advanced Bionics Corporation, Sylmar, Calif.

[21] Appl. No.: 09/140,033

[22] Filed: Aug. 26, 1998

Related U.S. Application Data

[60] Provisional application No. 60/056,055, Sep. 2, 1997.

[51] Int. Cl.[7] .................................................. A61N 1/04
[52] U.S. Cl. ............................................................ 607/137
[58] Field of Search ................................... 607/136, 137; 623/10

[56] References Cited

U.S. PATENT DOCUMENTS

| | | | |
|---|---|---|---|
| 4,819,647 | 4/1989 | Byers et al. | 128/642 |
| 4,832,051 | 5/1989 | Jarvik et al. | 128/784 |
| 4,898,183 | 2/1990 | Kuzma | 128/784 |
| 5,000,194 | 3/1991 | van den Honert et al. | 128/784 |
| 5,037,497 | 8/1991 | Stypulkowski | 156/245 |
| 5,443,493 | 8/1995 | Byers et al. | 607/137 |
| 5,545,219 | 8/1996 | Kuzma | 623/10 |
| 5,578,084 | 11/1996 | Kuzma et al. | 623/10 |
| 5,603,726 | 2/1997 | Schulman et al. | 607/57 |
| 5,645,585 | 7/1997 | Kuzma | 623/10 |
| 5,649,970 | 7/1997 | Loeb et al. | 607/57 |
| 5,653,742 | 8/1997 | Parker et al. | 607/137 |
| 5,667,514 | 9/1997 | Heller | 606/108 |

*Primary Examiner*—Scott M. Getzow
*Attorney, Agent, or Firm*—Bryant R. Gold

[57] ABSTRACT

An electrode array has a flexible carrier that, when viewed in cross-section, is much more flexible in a first direction than in a second direction orthogonal thereto. The flexible direction is the direction that allows the array to readily flex so as to assume the general spiral or circular shape of the scala tympani duct within the cochlea. The less-flexible direction is the direction that makes it difficult for the array to twist as it is inserted within the scala tympani duct. By placing the electrode contacts of the array on or near that surface of the array which becomes the inner surface of the spiral shape once implantation has occurred, the electrode array may be inserted within the cochlea using minimal force, yet twisting of the array becomes unlikely during insertion or thereafter. Four separate embodiments of the electrode array are described.

17 Claims, 6 Drawing Sheets

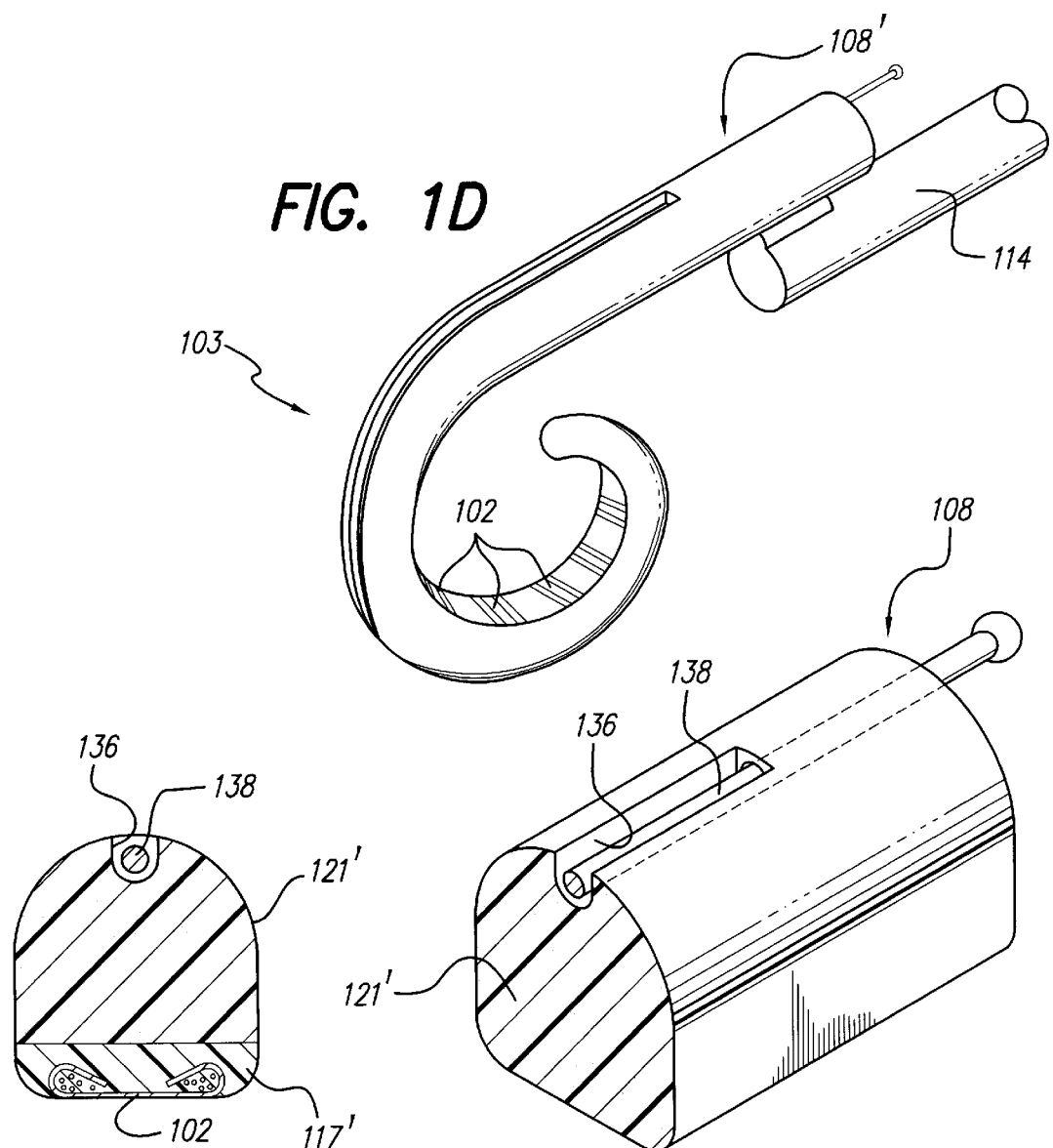
FIG. 1D
FIG. 3D
FIG. 2D
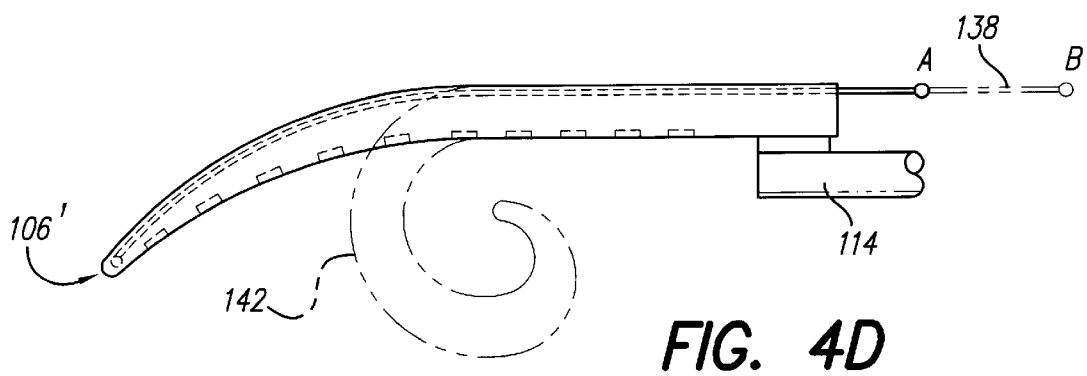
FIG. 4D

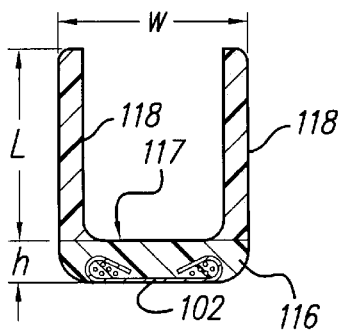
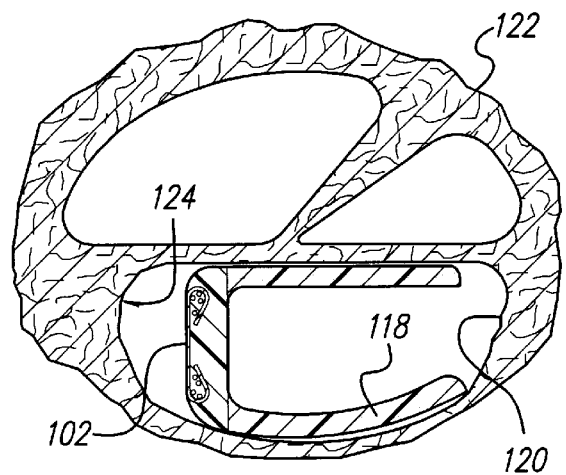
FIG. 4A              FIG. 5A
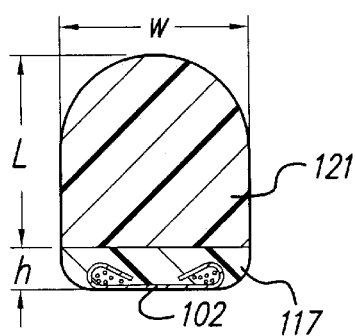
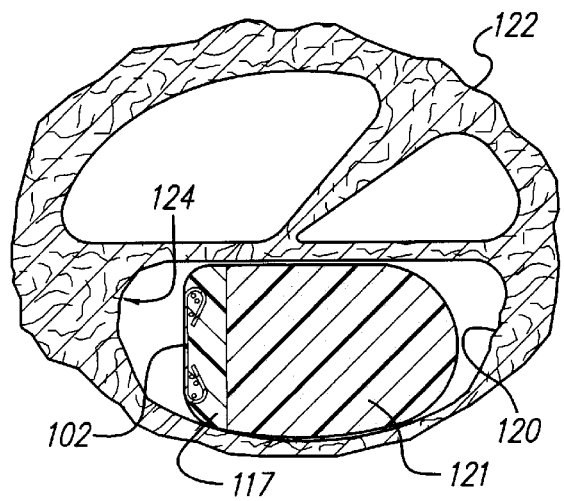
FIG. 4B              FIG. 5B

MODIOLUS-HUGGING COCHLEAR ELECTRODES

This application claims the benefit of U.S. Provisional Application Ser. No. 60/056,055, filed Sep. 2, 1997.

BACKGROUND OF THE INVENTION

The present invention relates to implantable stimulation devices, e.g., cochlear prosthesis used to electrically stimulate the auditory nerve, and more particularly to an electrode array designed to hug the modiolus so as to place electrode contacts of the electrode array in close proximity to the ganglion cells and thereby to the auditory nerve fibers.

Hearing loss, which may be due to many different causes, is generally of two types: conductive and sensorineural. Of these, conductive hearing loss occurs where the normal mechanical pathways for sound to reach the hair cells in the cochlea are impeded, for example, by damage to the ossicles. Conductive hearing loss may often be helped by use of conventional hearing aids, which amplify sound so that acoustic information does reach the cochlea and the hair cells. Some types of conductive hearing loss are also amenable to alleviation by surgical procedures.

In many people who are profoundly deaf, however, the reason for their deafness is sensorineural hearing loss. This type of hearing loss is due to the absence or the destruction of the hair cells in the cochlea which are needed to transduce acoustic signals into auditory nerve impulses. These people are unable to derive any benefit from conventional hearing aid systems, no matter how loud the acoustic stimulus is made, because their mechanisms for transducing sound energy into auditory nerve impulses have been damaged. Thus, in the absence of properly functioning hair cells, there is no way auditory nerve impulses can be generated directly from sounds.

To overcome sensorineural deafness, there have been developed numerous cochlear implant systems—or cochlear prosthesis—which seek to bypass the hair cells in the cochlear (the hair cells are located in the vicinity of the radially outer wall of the cochlea) by presenting electrical stimulation to the auditory nerve fibers directly, leading to the perception of sound in the brain and an at least partial restoration of hearing function. The common denominator in most of these cochlear prosthesis systems has been the implantation, into the cochlea, of electrodes which are responsive to a suitable external source of electrical stimuli and which are intended to transmit those stimuli to the ganglion cells and thereby to the auditory nerve fibers.

A cochlear prosthesis operates by direct electrical stimulation of the auditory nerve cells, bypassing the defective cochlear hair cells that normally transduce acoustic energy into electrical activity in such nerve cells. In addition to stimulating the nerve cells, the electronic circuitry and the electrode array of the cochlear prosthesis performs the function of the separating the acoustic signal into a number of parallel channels of information, each representing the intensity of a narrow band of frequencies within the acoustic spectrum. Ideally, each channel of information would be conveyed selectively to the subset of auditory nerve cells that normally transmitted information about that frequency band to the brain. Those nerve cells are arranged in an orderly tonotopic sequence, from high frequencies at the basal end of the cochlear spiral to progressively lower frequencies towards the apex. In practice, this goal tends to be difficult to realize because of the anatomy of the cochlea.

Over the past several years, a consensus has generally emerged that the scala tympani, one of the three parallel ducts that, in parallel, make up the spiral-shaped cochlea, provides the best location for implantation of an electrode array used with a cochlear prosthesis. The electrode array to be implanted in this site typically consists of a thin, elongated, flexible carrier containing several longitudinally disposed and separately connected stimulating electrode contacts, perhaps 6–30 in number. Such electrode array is pushed into the scala tympani duct to a depth of about 20–30 mm via a surgical opening made in the round window at the basal end of the duct. During use, electrical current is passed into the fluids and tissues immediately surrounding the individual electrical contacts in order to create transient potential gradients that, if sufficiently strong, cause the nearby auditory nerve fibers to generate action potentials. The auditory nerve fibers arise from cell bodies located in the spiral ganglion, which lies in the bone, or modiolus, adjacent to the scala tympani on the inside wall of its spiral course. Because the density of electrical current flowing through volume conductors such as tissues and fluids tends to be highest near the electrode contact that is the source of such current, stimulation at one contact site tends to activate selectively those spiral ganglion cells and their auditory nerve fibers that are closest to that contact site. Thus, there is a need for the electrode contacts to be positioned as close to the ganglion cells as possible. This means, in practice, that the electrode array, after implant, should preferably hug the modiolar wall, and that the individual electrodes of the electrode array should be positioned on or near that surface of the electrode array which is closest to the modiolar wall.

In order to address the above need, it is known in the art to make an intracochlear electrode array that includes a spiral-shaped resilient carrier which generally has a natural spiral shape so that it better conforms to the shape of the scala tympani. See, e.g., U.S. Pat. No. 4,819,647. The '647 U.S. patent is incorporated herein by reference.

It is also known in the art, as shown in applicant's prior patents, U.S. Pat. Nos. 5,545,219 and 5,645,585, to construct an electrode carrier from two initially straight members, a rod-like electrode carrier and a flexible rod-like positioning member. As shown in these patents, the two members extend in substantially parallel relation to and closely alongside each other, but are connected to each other only at their respective leading and trailing end regions. After implant, a pushing force is applied to the positioning member so that it is forced to assume an outwardly arched configuration relative to the electrode carrier, thereby forcing the electrode carrier into a close hugging engagement with the modiolus, thereby placing the electrode contacts of the electrodes in as close a juxtaposition to the cells of the spiral ganglion as possible. The '219 and '585 U.S. patents are also incorporated herein by reference.

Unfortunately, while the electrode array taught in the above-referenced '219 and '585 patents has the right idea, i.e., to force the electrode carrier into a close hugging engagement with the modiolus, it does so only through application of an additional pushing force which is applied to an electrode structure after it is already fully inserted into the cochlea. Such additional pushing force may easily cause damage to the delicate scala tympani. Moreover, the entire electrode array may twist during the insertion process, or when the additional pushing force is applied, thereby causing the electrode contacts to twist and/or be forced away from the modiolus, rather than in a hugging relationship therewith.

It is thus seen that improvements are still needed in cochlear electrodes, particularly to better assure that the electrode assumes a close hugging relationship with the modiolus, and to prevent rotation or twisting away of the electrode contacts from the modiolus during and after insertion.

SUMMARY OF THE INVENTION

The present invention addresses the above and other needs by providing an electrode array having a carrier that, when viewed in cross-section, is much more flexible in one direction than in a direction orthogonal thereto. The flexible direction is the direction that allows the array to readily flex so as to assume the general spiral shape of the scala tympani duct within the cochlea. The less-flexible direction is the direction that makes it difficult for the array to twist as it is inserted within the scala tympani duct. Hence, by placing the electrode contacts of the array on or near that surface of the array which becomes the inner surface of the spiral shape once implantation has occurred, the electrode array may be inserted within the cochlea using minimal force, yet twisting of the array is unlikely during insertion or thereafter. Moreover, by monitoring electrode impedance during and after insertion, feedback data is provided that indicates whether or not an optimum electrode position has been achieved.

Four separate embodiments of the improved electrode array of the present invention are contemplated.

In a first embodiment, referred to herein as the "low profile" electrode array, an electrode array is provided at a distal end of a cochlear electrode lead. The electrode array has a general U-shaped cross section. A base portion of the U-shaped cross section is made from a solid silastic material. In cross section, the base portion appears as a relatively thin ribbon-like material, having a relatively short height, and a relatively wide width. Electrical conductors are embedded within the base portion, and respectively connect exposed electrodes spaced along a bottom edge of the base portion to a suitable connector or exposed conductors at a proximal end of the lead, which proximal end of the lead is connected to an electrical stimulator device. The base material is thus very flexible in one direction (the direction corresponding to the thickness or height of the thin ribbon-like material when viewed in cross section), but not very flexible in a direction orthogonal thereto (i.e., in the direction corresponding to the relatively wide width of the ribbon-like material, when viewed in cross section). The legs of the U-shaped cross section are each made from a silastic sponge material which is readily compressible and flexible. Moreover, each of these legs has a length that is approximately equal to the transverse width of the scala tympani duct when viewed in cross section. Hence, when the array is inserted into the scala tympani, the base portion of the U-shaped cross-section array is positioned against the modiolus, and is maintained in this position by the legs of the U-shaped array. The spongy and flexible legs of the U-shaped cross section array further facilitate insertion of the array, while preventing twisting of the array during the insertion process.

A second embodiment of the electrode array, referred to as the "space filling" array, has a ribbon-like base portion that, in cross section, is substantially similar to or the same as the base portion of the U-shaped cross section array described above. However, a back portion of the array, when viewed in cross section, rather than comprising spongy and flexible legs, comprises a solid portion made from a silastic sponge material that is both flexible and compressible. (It is as though the channel of U-shaped cross section has been filled in.) In cross section, this second embodiment, or space-filling embodiment, thus substantially fills the scala tympani duct, with the ribbon-like base portion being positioned and held against the modiolus by the flexible and compressible back portion of the array.

A third embodiment, referred to as the "programmable shape" embodiment, comprises an electrode array having a substantially U-shaped cross section, similar to the "low profile" embodiment described above. The channel formed by the U-shape cross section has a tube placed therein. A programming wire is placed in a lumen of the tube. A distal end of the programming wire is securely attached to a distal end of the electrode array. During insertion, a distal end of the tube, which lies within the channel of the U-shaped cross section array, extends beyond the distal end of the array a prescribed amount, e.g., 7 mm, while the programming wire extends from the proximal end of the tube about 3 mm. After insertion to the appropriate depth, the programming wire is pulled from the proximal end of the tube. The pulling of the programming wire may be a full stroke distance, e.g., about 7 mm, which forces the distal end of the tube against the distal end of the array, or some intermediate stroke distance, e.g., 3–4 mm, which forces the distal end of the tube towards the distal end of the array, but does not bring the two distal ends together. Whether the programming wire is pulled a full stroke or intermediate stroke distance, the effect is to force the U-shaped array inwardly within the scala tympani duct so that the base portion of the U-shaped array assumes a close hugging engagement with the modiolus. Advantageously, by monitoring electrode impedance as the pull stroke is applied to the programming wire, an optimum electrode position can generally be found.

A fourth embodiment, referred to as the "precurved with opener" embodiment, comprises an electrode array having a cross section that is substantially similar to the space-filling embodiment described above. That is, the array includes, in cross section, a base ribbon-like portion that is made from a solid silastic material so that it is readily flexible in one direction, but not in a direction orthogonal thereto. The base ribbon-like portion is backed with a filled body portion made from a flexible, solid spongy material. The array is made so that it naturally assumes a spiral shape. A small groove is placed along the back side of the body portion. An insertion wire is placed within the groove and a distal end of the insertion wire is permanently attached to a distal end of the array. By pulling on the insertion wire, the natural spiral shape of the array may be straightened. By releasing the insertion wire, i.e., by removing the pulling force, the array returns to its natural spiral shape. Thus, during insertion, some pulling force is applied to the insertion wire to straighten the array and make initial insertion easier. As the array is inserted deeper into the cochlea, the pulling force is gradually released, thereby allowing the array to gradually assume its natural spiral shape. After insertion to the desired depth, the pulling force on the insertion wire is completely released, and the array assumes its natural spiral shape, holding its base portion against the modiolus.

It is thus a feature of the present invention to provide an electrode array for use with a cochlear stimulator that is easy to insert within the cochlea, and that resists twisting.

It is a further feature of the invention to provide an electrode array that hugs the modiolus, placing contact faces of the electrodes used within such array in close proximity to ganglion cells of the auditory nerve.

BRIEF DESCRIPTION OF THE DRAWINGS

The above and other aspects, features and advantages of the present invention will be more apparent from the following more particular description thereof, presented in conjunction with the following drawings wherein:

FIG. 1D is a schematic representation of an electrode array made in accordance with a "precurved with opener" embodiment of the invention;

FIG. 2D is a perspective sectional view of the "precurved with opener" electrode array of FIG. 1D;

FIG. 3D is a sectional view of the "precurved with opener" electrode array of FIG. 1D and FIG. 2D;

FIG. 4A is a sectional view of the "low profile" electrode array of FIGS. 1A, 2A, and 3A;

FIG. 4B is a sectional view of the "space filling" embodiment of the electrode array of FIGS. 1B, 2B and 3B;

FIG. 4D schematically shows a side view of the two positions assumed by the "precurved with opener" electrode array of FIGS. 1D, 2D and 3D;

FIG. 5A is a cross section of the cochlea, showing the manner in which the "low profile" electrode array fits within the scala tympani;

FIG. 5B is a cross section of the cochlea, illustrating the manner in which the "space filling" electrode array fits within the scala tympani.

Corresponding reference characters indicate corresponding components throughout the several views of the drawings.

DETAILED DESCRIPTION OF THE INVENTION

Figure 1A:
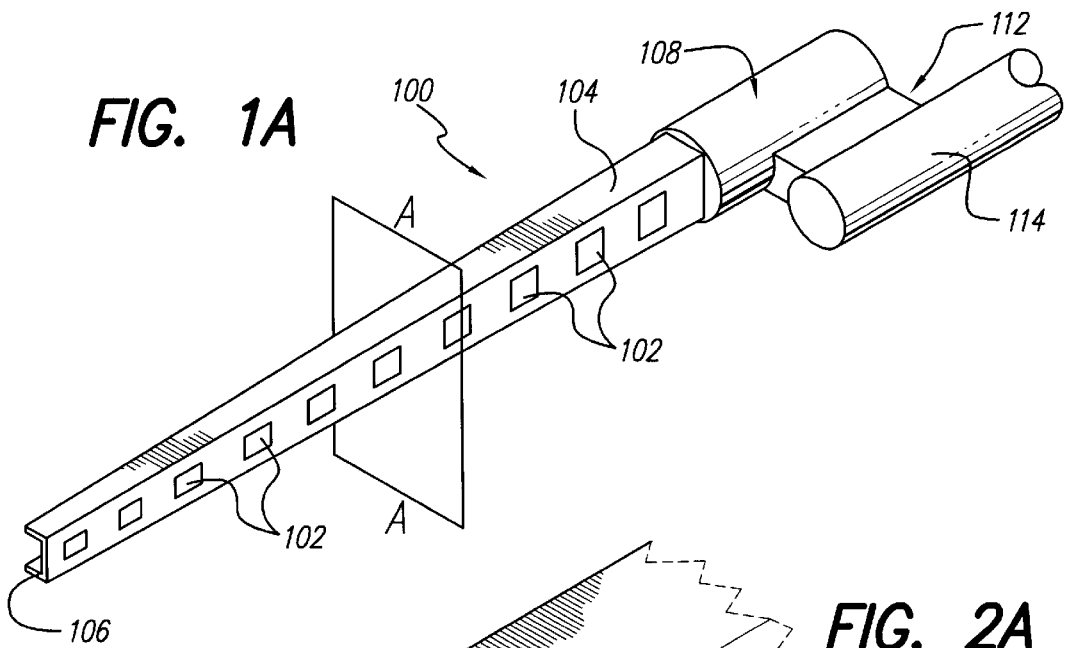
FIG. 1A is a schematic representation of a "low profile" electrode array made in accordance with the invention.
Figure 2A:
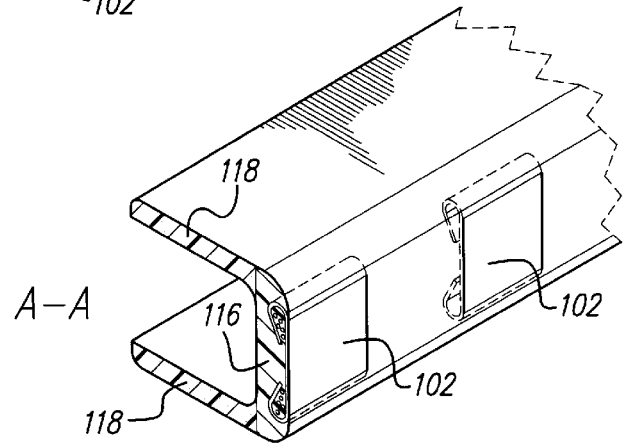
FIG. 2A is a perspective sectional view of the "low profile" electrode array taken through the plane A—A of FIG. 1A.

The following description is of the best mode presently contemplated for carrying out the invention. This description is not to be taken in a limiting sense, but is made merely for the purpose of describing the general principles of the invention. The scope of the invention should be determined with reference to the claims.

As indicated above, the present invention relates to an improved electrode array, of which four embodiments are disclosed herein. Variations of these four embodiments could, of course, also be used to provide the same advantageous features of the invention. In the figures, an "A" suffix refers to a drawing that relates to the "low profile" embodiment electrode array. Thus, FIGS. 1A, 2A, 3A, 4A and 5A all relate to and show various features of the low profile electrode embodiment. Similarly, a "B" suffix refers to a drawing that relates to the "space filling" embodiment; a "C" suffix refers to a drawing that shows the ""programmable shape" embodiment; and a "D" suffix refers to a drawing that relates to the "precurved with opener" embodiment.

The materials from which the leads and electrode arrays of the present invention are made, for all the embodiments disclosed herein and any variations thereof, may be any suitable material as is known in the art, or as is subsequently developed. In general, the conductive electrode contacts and wires connected thereto are made from platinum or a platinum alloy or other suitable bio-compatible metals. The carrier in which the wires and electrodes are embedded may be made from Silastic silicone plastic or an equivalent bio-compatible material. The leads and electrode arrays are typically made using a suitable molding process, e.g., as disclosed in U.S. Pat. No. 4,819,647, previously incorporated herein by reference.

Turning, then, to FIGS. 1A, 2A, 3A, 4A and 5A, the "low profile" electrode embodiment of the invention will be described. As seen in these figures, the "low profile" embodiment comprises an electrode array 100 that provides a plurality of spaced-apart individual electrode contacts 102 carried on an elongate silastic carrier 104. The carrier 104 is generally tapered so facilitate its insertion into the cochlea. That is, a distal tip 106 of the array 100 has a small cross sectional area compared with the cross sectional area of a proximal end 108 of the array 100. An elbow 112, typically a right-angle elbow, located near the proximal end 108 of the array 100, connects the array 100 to a lead body 114. The lead body 114 contains individual electrical conductors, embedded in silastic or other material, that connect to an electrical stimulation device (not shown), as is known in the art. The elbow 112 facilitates insertion of the array 100 into the cochlea using an insertion tool of the type described in U.S. Pat. No. 5,443,493, or an equivalent tool. The '493 patent is incorporated herein by reference.

Figure 3A:
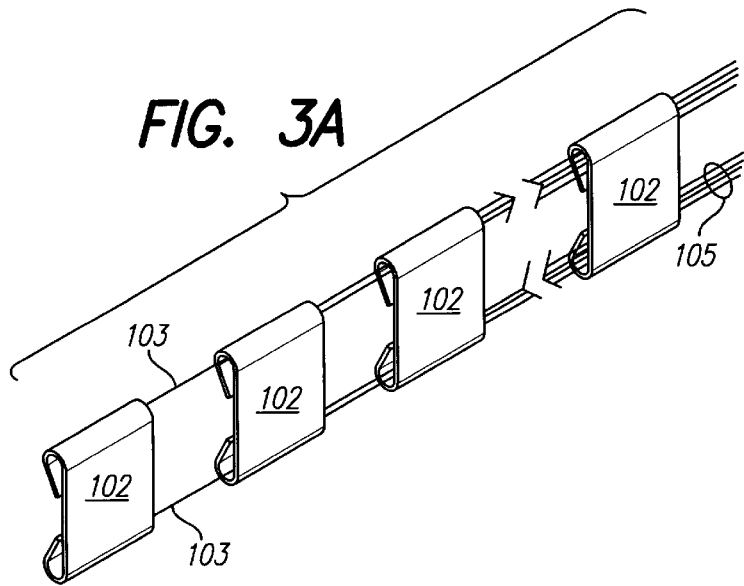
FIG. 3A illustrates the electrode contacts and conductors that are included within the ribbon-like base portion of the "low profile" electrode array of FIGS. 1A and 2A.
Figure 1B:
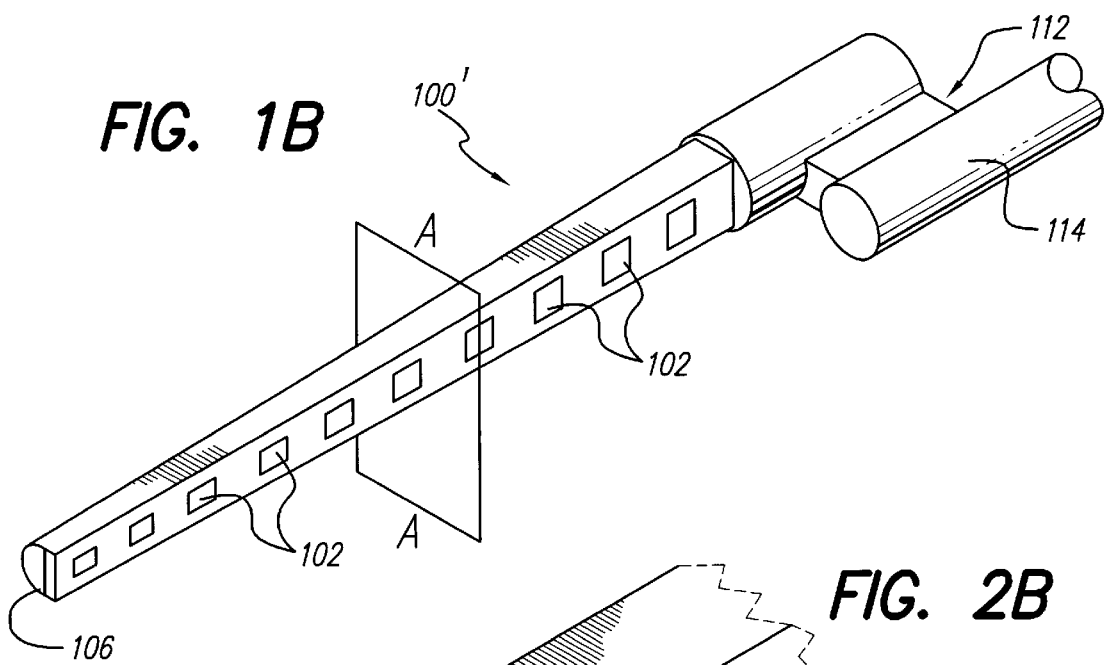
FIG. 1B is a schematic representation of an electrode array made in accordance with a "space filling" embodiment of the invention.
Figure 2B:
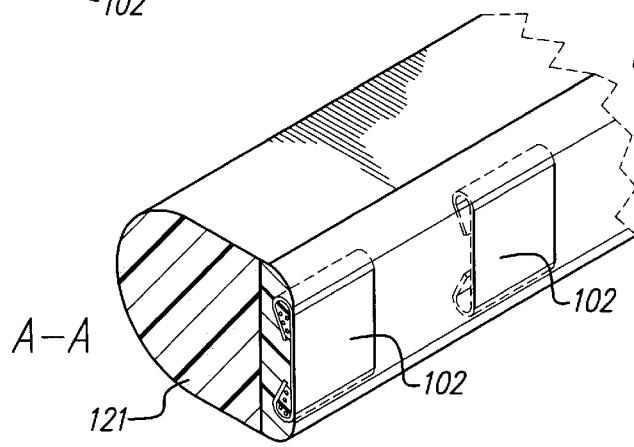
FIG. 2B is a perspective sectional view of the "space-filling" electrode array taken through the plane A—A of FIG. 1B.
Figure 3B:
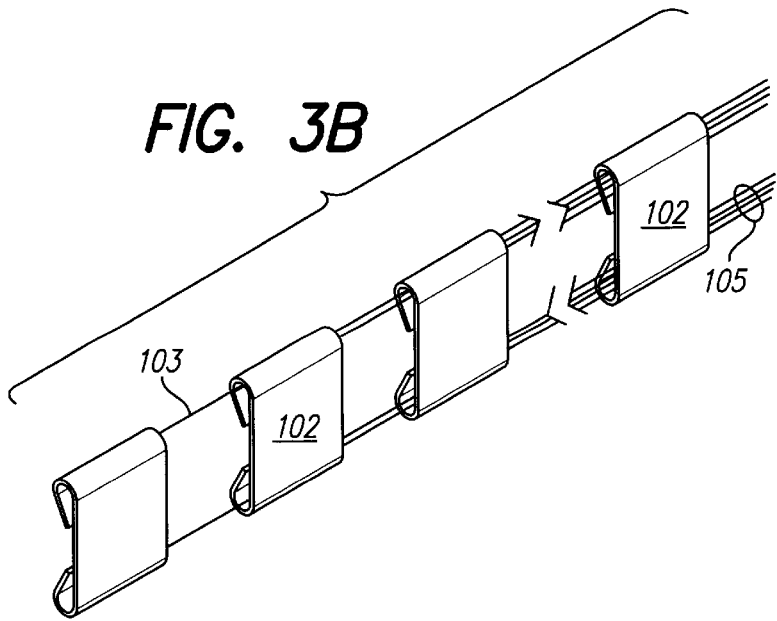
FIG. 3B shows the electrode contacts and conductors that are included within the ribbon-like base portion of the "space-filling" electrode array of FIG. 1B and FIG. 2B.
Figure 1C:
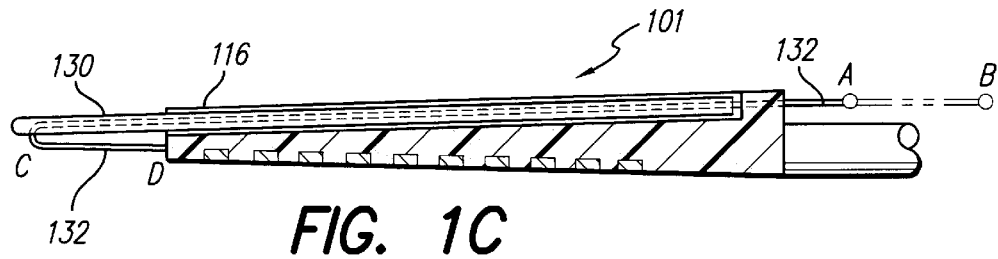
FIG. 1C is a schematic sectional representation of an electrode array made in accordance with a "programmable shape" embodiment of the invention.
Figure 2C:
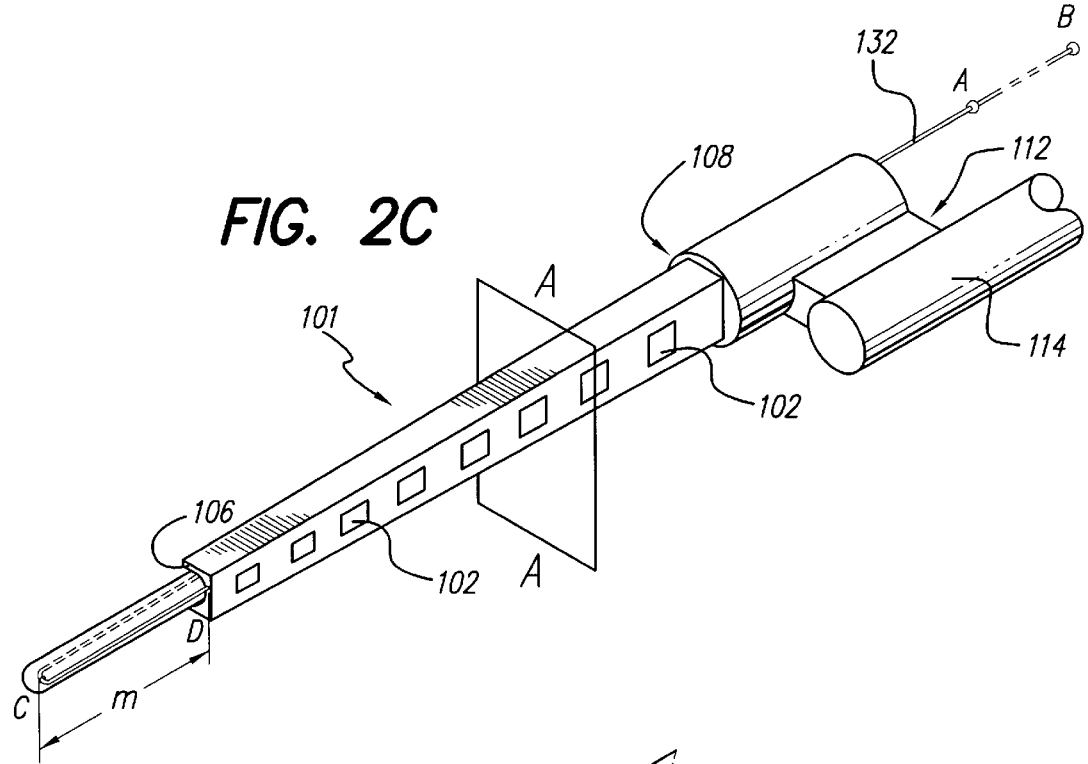
FIG. 2C is a schematic representation of the "programmable shape" electrode array of FIG. 1C.
Figure 3C:
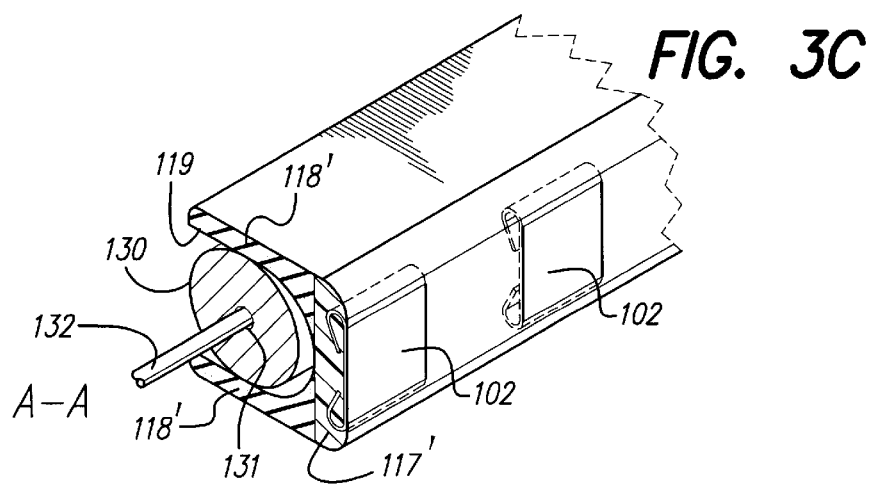
FIG. 3C depicts a perspective sectional view of the "programmable shape" electrode array of FIG. 1C and FIG. 2C.

The electrode contacts 102, as seen best in FIG. 3A, comprise flat strips of a suitable bio-compatible metal, such as platinum, curved at the edges thereof in order to crimp onto and electrically connect with individual insulated small conductive wires 103. As the wires 103 wend their way towards the proximal end 108 of the array, they accumulate in numbers to form a bundle 105 of wire conductors, each of which is electrically insulated from the others.

The electrode/wire structure shown in FIG. 3A is embedded within a suitable solid silastic material 116 using, e.g., a molding process. A surface of the individual electrode contacts 102 is left exposed within the solid silastic material 116, thereby enabling this exposed surface to function as the electrode contact that is to be placed adjacent the ganglion cells in the modiolus when the lead is inserted into the scala tympani duct.

The silastic material 116 into which the electrodes 102 and wires 103 are embedded thus form a ribbon-like cable having a relatively short height "h" and a relatively long width "w", as shown best in FIG. 4A. In this manner, the ribbon-like cable is readily flexible (i.e., can easily bend to form a spiral) in the direction of the short height "h"; but is not very flexible (i.e., cannot easily bend or twist) in the direction of the long width "w".

The ribbon-like portion comprising the electrodes 102 and wires 103, embedded into the solid silastic material 116, form a base portion 117 of the array 100. Side extensions 118 extend rearwardly from the base portion 117. In cross section, as seen best in FIGS. 2A and 4A, the array 100 thus assumes a U-shape. The side extensions 118, also referred to as the "legs" of the U-shaped cross section, are made from a silastic sponge material that is more flexible and compressible than is the solid silastic material from which the base portion 117 is made. Each side extension or leg 118 extends up from the base portion a length "L". The length dimension "L" and the width dimension "w", both vary gradually from larger values at the proximal end 112 of the array 100 to smaller values at the distal end 106 in order to give the array its desired tapered shape, as shown generally in FIG. 1A.

The dimensions "w" and "L" are selected so that the overall taper or cross-sectional size of the array 100 approximates (or is slightly smaller than) the cross-sectional size of the scala tympani duct. Thus, as seen best in FIG. 5A, when the array 100 is inserted into the scala tympani duct 120 of the cochlea 122, the electrodes 102 are spaced closely to the modiolus 124, and are maintained in this position by the extension or length of the flexible legs 118. Because the legs 118 are very flexible and compressible, they can easily bend and flex, as required, during the insertion process. However, because of the positioning of the legs 118, and the relative stiffness of the base portion 117 in the direction orthogonal to the direction of the spiral, it is not easy for the array 100 to twist or otherwise become positioned incorrectly within the cochlea 122.

Thus, by way of summary and as shown in FIGS. 1A, 2A, 3A, 4A and 5A, it is seen that the "low profile" electrode array 100 has a general U-shaped cross section. The base portion 117 of the U-shaped cross section is made from a solid silastic material 116. In cross section, the base portion 117 appears as a relatively thin ribbon-like material, having a relatively short height "h", and a relatively wide width "w". Electrical conductors 103 are embedded within the base portion 117, and respectively connect to exposed electrodes 102 spaced along a bottom edge of the base portion. The base portion is thus very flexible in one direction (the direction corresponding to the thickness or height "h" of the thin ribbon-like material 116 when viewed in cross section), but not very flexible in a direction orthogonal thereto (i.e., in the direction corresponding to the relatively wide width "w" of the ribbon-like material, when viewed in cross section). The legs 118 of the U-shaped cross section are each made from a silastic sponge material which is readily compressible and flexible. Moreover, each of these legs has a length "L" that is approximately equal to the transverse width of the scala tympani duct 120 when viewed in cross section. Hence, when the array is inserted into the scala tympani, the base portion 117 of the U-shaped cross-section array is positioned against the modiolus 124, and is maintained in this position by the legs of the U-shaped array. The spongy and flexible legs of the U-shaped cross section array further facilitate insertion of the array, while preventing twisting of the array during the insertion process.

Turning next to FIGS. 1B, 2B, 3B, 4B and 5B, a "space filling" embodiment of an electrode array 100', is illustrated.

In general, the space-filling array 100' is the same as the "low profile" array 100 described above, and the description present above in connection with the array 100 applies equally to the space-filling array 100'. The one key difference between the array 100' and the array 100 is that instead of flexible legs 118 on the back of the base portion 117, there is a spongy, flexible and compressible back portion 121. This backing portion 121 is made from a silastic spongy material that is both flexible and compressible. Conceptually, it is as though the channel of U-shaped cross section between the legs 118 of the low profile embodiment 100, described above, is filled in with additional spongy and compressible silastic material. The back portion 121 extends rearwardly from the base portion 117 a distance "L", and has a width "w". As seen in the cross-sectional view of FIG. 4B, these general dimensions are tapered to provide smooth round surfaces for the array 100'. In cross section, this space-filling embodiment 100' thus substantially fills the scala tympani duct 120, as shown best in FIG. 5B, with the ribbon-like base portion 117 being positioned and held against the modiolus 124 by the flexible and compressible back portion 121.

Next, with reference to FIGS. 1C, 2C, 3C, 4C and 5C, a "programmable shape" array 101 is illustrated. As seen in these figures, the array 101 includes a flexible silastic carrier having a general U-shaped cross section having a base portion 117' and side extensions, or legs, 118'. Electrode contacts 102 are embedded within the base portion 117' as previously described. Within a channel 119 formed between the extensions or legs 118' there is placed a tube 130. The tube 130 fits snugly within the channel 119. A distal end of the tube 130, at point "C", initially extends beyond the distal end 106 of the array 101 a distance "m".

A lumen 131 passes through the center of the tube 130. A programming wire 132 passes all the way through the lumen 131 from a distal end of the tube 130 at point "C" to a proximal end at point "A". The wire 132 initially extends from the tube 130 at the distal end "C" and folds back and joins the distal end of the array 101 at point "D".

Figure 4C:
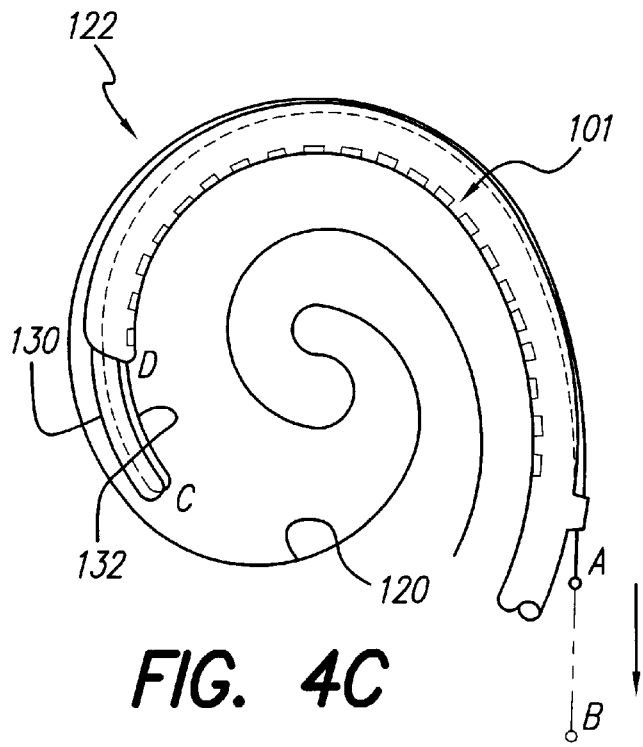
FIG. 4C schematically illustrates insertion of the "programmable shape" electrode array prior to seating the array against the modiolus.
Figure 5C:
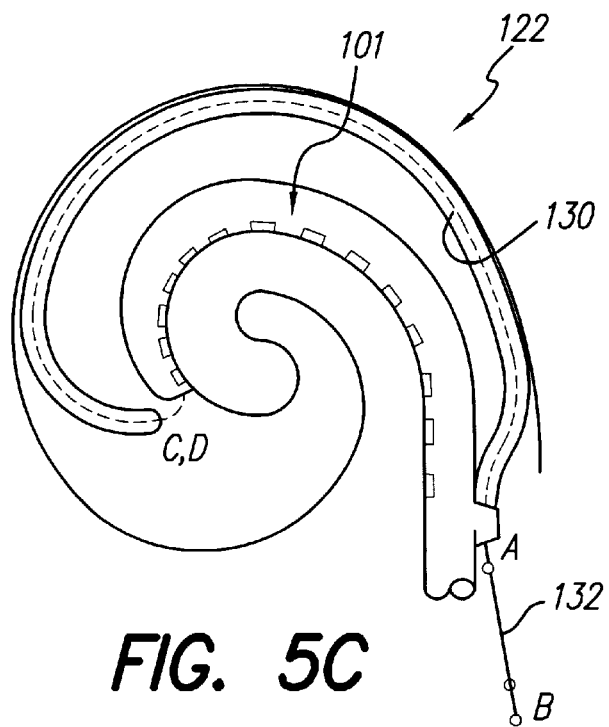
FIG. 5C schematically illustrates insertion of the "programmable shape" electrode array after seating the array against the modiolus.

When the array 101 is first inserted into the cochlea 122, as seen best in FIG. 4C, the tube 130 assumes its initial position and extends beyond the distal tip D of the array 101. After the array 101 has been inserted to its proper depth within the scala tympani duct 120 of the cochlea, the programming wire 132 is pulled an appropriate amount so that a proximal end of the wire, at point "A", is pulled towards point "B". The point "A" typically extends beyond the proximal end of the tube 130 about 3–4 mm. Point "B", represents a full stroke movement of the wire 132, and typically is about another 7 mm further than point "A". A full stroke pull of the programming wire 132, i.e., pulling the wire from point "A" to point "B", pulls point "C" at the distal end of the tube 130 to point "D" at the distal end of the array 101. This action, in turn, forces the array 101 radially inwardly within the spiral-shaped scala tympani duct 120 so that it hugs the modiolus wall, as desired, while the tube 130 remains pushed against the outer wall of the scala tympani duct.

A partial stroke pull of the programming wire 132, i.e., pulling the wire from point "A" to some intermediate point that is not as far as point "B", has the same effect of forcing the array 101 radially inwardly within the spiral-shaped scala tympani duct, but not with the same force, and not to the same degree. An important feature of the invention is that this ability to pull the programming wire 132 a lesser or greater amount allows the array 101 to be optimally positioned within the scala tympani duct. The optimal position is determined using any suitable test or monitoring technique.

Typically, while such pulling is performed, the impedance of the electrodes is monitored, e.g., using an implantable cochlear stimulator (ICS) that has the ability to monitor electrode impedance, such as that disclosed in U.S. Pat. No. 5,603,726, incorporated herein by reference.

For the array 101 shown in FIGS. 1C, 2C, 3C, 4C and 5C, the material from which the base portion 117' and the side extensions 118' are made may be a spongy or rigid silastic material, or other suitable bio-compatible material. The distance "m" by which the tube 130 initially extends beyond the distal end 106 of the array 101 will typically comprise about 7 mm. The wire 132 may be made from platinum, or other suitable bio-compatible material. It is noted that the wire 132 need not be electrically conductive, so it can also be made from numerous non-conductive synthetic or natural fiber-like substances.

Thus, in summary, it is seen that the "programmable shape" embodiment, shown in FIGS. 1C, 2C, 3C, 4C and 5C, comprises an electrode array 101 having a substantially U-shaped cross section. The channel formed by the U-shape cross section has a tube 130 placed therein. A programming wire 132 is placed through the lumen 131 of the tube. A distal end "C" of the programming wire 132 is securely attached to a distal end "D" of the electrode array 101. During insertion, a distal end of the tube 130, which fits snugly within the channel 119 of the U-shaped cross section array, extends beyond the distal end of the array a prescribed amount. After insertion to the appropriate depth, the programming wire 132 is pulled from a first proximal end position "A" to a second proximal end position "B". The pulling force tends to pull the distal end of the tube "C" against the distal end "D" of the array, which has the effect of forcing the U-shaped array 101 inwardly within the scala tympani duct 120 so that the base portion 117' of the U-shaped array 101 assumes a close hugging engagement with the modiolus.

Next, turning to FIGS. 1D, 2D, 3D and 4D, a "precurved with opener" embodiment of an electrode array 103 is illustrated. This array 103 comprises an electrode array having a cross section (FIG. 3D) that is substantially similar to the space-filling embodiment 100' described above. That is, the array 103 includes, in cross section, a base ribbon-like portion 117' that is made from a solid silastic material so that it is readily flexible in one direction, but not in a direction orthogonal thereto. The base ribbon-like portion 117' is backed with a filled body portion 121' made from a flexible, solid spongy material.

Unlike the space-filling embodiment 100', the array 103 is made so that it naturally assumes a spiral shape. A small groove 136 is placed along the back side of the body portion 117'. An insertion wire 138 is placed within the groove 136. The groove is closed near the proximal end 108' of the array to keep or maintain the wire 138 within the groove. A distal end of the insertion wire 138 is permanently attached to a distal end 106' of the array 103. By pulling on the insertion wire 138, which is able to slide within the groove 136, the natural spiral shape of the array 103 may be straightened. By releasing the insertion wire 138, i.e., by removing the pulling force, the array 103 returns to its natural spiral shape. Thus, during insertion, some pulling force is applied to the insertion wire 138 to straighten the array and make initial insertion easier and to assist in optimal positioning of the electrode array. As the array 103 is inserted deeper into the cochlea, the pulling force is gradually released, thereby allowing the array to gradually assume its natural spiral or curved shape, as shown by the dashed lines 142. After insertion to the desired depth, the pulling force on the insertion wire 138 is partially or completely released, thereby positioning the array in an optimum position within the scala tympani duct, wherein the array assumes its natural spiral shape, or something close thereto, holding its base portion 117' near or against the modiolus, which is the desired result. The optimum position may be determined using any suitable testing or monitoring technique, e.g., measuring electrode impedance, both during and after implantation, as described above. The back portion 121' of the array 103 helps assure that the base portion 117' remains in its desired orientation, hugging the modiolus, and not twisting.

As described above, it is thus seen that the present invention provides various embodiments of an electrode array for use with a cochlear stimulator, all of which are easy to insert within the cochlea, and which resist twisting. It is further seen that the invention provides various embodiments of an electrode array, all of which hug the modiolus, placing contact faces of the electrodes used within such arrays in close proximity to ganglion cells of the auditory nerve.

While the invention herein disclosed has been described by means of specific embodiments and applications thereof, numerous modifications and variations could be made thereto by those skilled in the art without departing from the scope of the invention set forth in the claims.

What is claimed is:

1. An electrode array for use with a stimulation device comprising:

a flexible carrier that, when viewed in cross-section, is much more flexible in a first direction than in a second direction orthogonal to the first direction;

a plurality of spaced-apart electrode contacts embedded within the flexible carrier, a portion of each contact being exposed at a first surface of the carrier;

the first surface of the carrier comprising that surface which assumes a curved radius when the flexible carrier is flexed in the first direction;

wherein the flexible carrier has a U-shaped cross section having a base portion and side extensions, and wherein the base portion comprises a solid material wherein the electrodes are embedded, and wherein the base portion has a height "h" and a width "w", where w is much greater than h, whereby the base portion forms a ribbon-like cable that readily flexes in the first direction, the direction of the height h, but that does not readily flex in the second direction, the direction of the width w; and each side extension comprises a flexible wall that extends rearwardly from the base portion a prescribed distance, the prescribed distance comprising a distance that is slightly less than a cross-sectional lateral distance across a duct within which the electrode array is to be inserted.

2. The electrode array of claim 1 further comprising:

a tube positioned within a channel formed between the side extensions of the U-shaped cross section of the flexible carrier;

a lumen that passes through the tube;

a wire that slidably passes through the lumen;

a distal end of the tube extending beyond a distal end of the carrier a prescribed distance; and a distal end the wire that passes through the lumen being attached to the distal end of the carrier;

whereby the electrode array may be inserted into a curved duct, and after insertion a pulling force may be applied to a proximal end of the wire, thereby pulling the distal end of the tube towards the distal end of the carrier, thereby causing the base portion of the carrier to hug an inner radius of the curved duct.

3. An electrode array for use with a stimulation device comprising:
   a flexible carrier that, when viewed in cross-section, is much more flexible in a first direction than in a second direction orthogonal to the first direction;
   a plurality of spaced-apart electrode contacts embedded within the flexible carrier, a portion of each contact being exposed at a first surface of the carrier;
   the first surface of the carrier comprising that surface which assumes a curved radius when the flexible carrier is flexed in the first direction;
   wherein the flexible carrier has a rectangular cross sectional shape with smoothed corners made up of a ribbon-like base portion and a back portion, and wherein
   the base portion comprises a solid material wherein the electrodes are embedded, and wherein the base portion has a height "h" and a width "w", where w is much greater than h, whereby the base portion forms a ribbon-like cable that readily flexes in the first direction, the direction of the height h, but that does not readily flex in the second direction, the direction of the width w; and
   the back portion comprises a spongy, flexible and compressible material that extends rearwardly from the base portion a prescribed distance, the prescribed distance comprising a distance that is less than a cross-sectional lateral distance across a duct within which the electrode array is to be inserted.

4. The electrode array of claim 3 wherein the flexible carrier is formed to naturally assume a curved shape.

5. The electrode array of claim 4 wherein the back portion of the flexible carrier has a groove formed therein into which a wire is placed, the groove having keeper means for maintaining the wire in the groove, a distal end of the wire being attached to a distal end of the array, whereby a pulling force may be applied to a proximal end of the wire in order to straighten the naturally curved array.

6. The electrode array of claim 3 wherein the electrode array comprises a cochlear electrode array having a flexible carrier sized for insertion into a human cochlea.

7. An electrode array comprising
   a flexible carrier that when viewed in cross-section, is more flexible in a first direction than in a second direction orthogonal thereto;
   the first direction comprising the direction that allows the array to readily flex so as to assume the general spiral shape of the scala tympani duct within a human cochlea;
   the second direction comprising the direction that makes it difficult for the electrode array to twist when it is inserted within a scala tympani duct;
   spaced-apart electrode contacts placed on an inner surface of the flexible carrier, the inner surface comprising that surface of the flexible carrier which becomes the inner surface of the spiral shape when the electrode array is inserted within the scala tympani duct;
   means embedded within the flexible carrier for making electrical contact with the spaced-apart electrode contacts;
   whereby the electrode array is insertable within the scala tympani duct using minimal force, yet twisting of the electrode array becomes unlikely during insertion or thereafter, and
   wherein the flexible carrier has a U-shaped cross section having a base portion and side extensions, and wherein
   the base portion comprises a solid material wherein the electrodes are embedded, and wherein the base portion has a height "h" and a width "w", where w is much greater than h, whereby the base portion forms a ribbon-like cable that readily flexes in the direction of the height h, but that does not readily flex in the direction of the width w; and
   each side extension comprises a flexible wall that extends rearwardly from the base portion a prescribed distance, the prescribed distance comprising a distance that is less than a cross-sectional lateral distance across the scala tympani duct within which the electrode array is adapted to be inserted.

8. The electrode array of claim 7 further comprising:
   a tube positioned within a channel formed between the side extensions of the U-shaped cross section of the flexible carrier;
   a lumen that passes through the tube;
   a wire that slidably passes through the lumen;
   a distal end of the tube extending beyond a distal end of the flexible carrier a prescribed distance; and
   a distal end the wire that passes through the lumen being attached to the distal end of the flexible carrier;
   whereby the electrode array may be inserted into the spiraling or curved scala tympani duct, and after insertion a pulling force may be applied to a proximal end of the wire, thereby pulling the distal end of the tube towards the distal end of the carrier, thereby causing the base portion of the carrier to hug an inner radius of the spiraling or curved scala tympani duct.

9. An electrode array comprising
   a flexible carrier that when viewed in cross-section is more flexible in a first direction than in a second direction orthogonal thereto;
   the first direction comprising the direction that allows the array to readily flex so as to assume the general spiral shape of the scala tympani duct within a human cochlea;
   the second direction comprising the direction that makes it difficult for the electrode array to twist when it is inserted within a scala tympani duct;
   spaced-apart electrode contacts placed on an inner surface of the flexible carrier, the inner surface comprising that surface of the flexible carrier which becomes the inner surface of the spiral shape when the electrode array is inserted within the scala tympani duct;
   means embedded within the flexible carrier for making electrical contact with the spaced-apart electrode contacts;
   whereby the electrode array is insertable within the scala tympani duct using minimal force, yet twisting of the electrode array becomes unlikely during insertion or thereafter, and
   wherein the flexible carrier has a generally rectangular cross sectional shape with smoothed corners and is made up of a ribbon-like base portion and a back portion, and wherein
   the base portion comprises a solid material within which the electrodes are embedded, and wherein the base portion has a height "h" and a width "w", where w is much greater than h, whereby the base portion forms a ribbon-like cable which readily flexes in the direction of the height h, but which does not readily flex in the direction of the width w; and wherein the back portion comprises a flexible and compressible material that extends rearwardly from the base portion a prescribed distance, the prescribed distance comprising a distance that is less than a cross-sectional lateral distance across the scala tympani duct.

10. The electrode array of claim 9 wherein the flexible carrier is formed to naturally assume a curved shape.

11. The electrode array of claim 10 wherein the back portion of the flexible carrier has a groove formed therein into which a wire is placed, the groove having keeper means for maintaining the wire in the groove, a distal end of the wire being attached to a distal end of the electrode array, whereby a pulling force applied to a proximal end of the wire straightens the naturally curved electrode array.

12. A method of making an implantable electrode array adapted for insertion into the curved scala tympani duct of a human cochlea, the method comprising:

forming a flexible carrier having a base portion and a back portion, embedding spaced-apart electrode contacts within the base portion, embedding wires within the base portion that make electrical contact with the spaced-apart electrode contacts;

forming the base portion from a solid flexible material that has a height "h" and a width "w", where w is much greater than h, whereby the base portion forms a ribbon-like cable which readily flexes in the direction of the height h, but which does not readily flex in the direction of the width w; and forming the back portion from a flexible material that extends rearwardly from the base portion a prescribed distance, the prescribed distance comprising a distance that is less than a cross-sectional lateral distance across the scala tympani duct.

13. The method of claim 12 wherein the step of forming the back portion comprises forming the back portion from side extensions so that the electrode array has a U-shaped cross section, each side extension comprising a flexible wall that extends rearwardly from the base portion a prescribed distance, the prescribed distance comprising a distance that is less than a cross-sectional lateral distance across the scala tympani duct within which the electrode array is adapted to be inserted.

14. The method of claim 12 wherein the step of forming the back portion comprises forming the back portion from a flexible and compressible material that extends rearwardly from the base portion a prescribed distance, the prescribed distance comprising a distance that is less than a cross-sectional lateral distance across the scala tympani duct.

15. A cochlear electrode array comprising:

a flexible carrier that naturally assumes a curved shape, the flexible carrier having characteristics that, when viewed in cross-section, make it more flexible in a first direction than in a second direction orthogonal thereto, wherein the first direction comprises the direction that allows the array to readily flex so as to assume the general spiral shape of a human cochlea, and wherein the second direction comprises the direction that makes it difficult for the electrode array to twist when it is inserted within the cochlea;

a plurality of spaced-apart electrode contacts carried on the flexible carrier, wherein each electrode contact has an exposed portion on an inner surface of the flexible carrier, wherein the inner surface comprises that side of the flexible carrier that becomes the inner surface of the spiral shape when the electrode array is inserted within the cochlea;

conductive wires embedded within the flexible carrier that make respective electrical contact with each of the plurality of spaced-apart electrode contacts; and an insertion wire that facilitates straightening the naturally curved flexible carrier when the electrode array is inserted within the cochlea.

16. The cochlear electrode array of claim 15 wherein the insertion wire is carried within the flexible carrier, and wherein the insertion wire, when pulled, straightens the naturally curved flexible carrier to facilitate insertion of the electrode array within the cochlea, and when released, allows the flexible carrier to assume its naturally curved shape, thereby positioning the electrode contacts closer to the inner surface of the spiraling cochlea.

17. The cochlear electrode array of claim 15 wherein the flexible carrier is made up of a ribbon-like base portion and a back portion, and wherein the base portion comprises a ribbon-like portion within which the electrodes and conductive wires are embedded, and wherein the base portion, when viewed in cross section, has a height h and a width w, and forms a ribbon-like cable which readily flexes in the direction of the height h, but which does not readily flex in the direction of the width w; and wherein the back portion comprises a flexible material that extends rearwardly from the base portion and has a channel formed therein into which the insertion wire may be placed.

* * * * *